United States Patent
Kenney et al.

(10) Patent No.: US 9,752,111 B2
(45) Date of Patent: Sep. 5, 2017

(54) CELL CULTURE SYSTEM WITH MANIFOLD

(75) Inventors: David A. Kenney, Lunenberg, MA (US); Gregory R. Martin, Acton, ME (US); Allison J. Tanner, Portsmouth, NH (US); Joseph C. Wall, Southborough, MA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/712,814

(22) Filed: Feb. 25, 2010

(65) Prior Publication Data

US 2010/0216229 A1    Aug. 26, 2010

Related U.S. Application Data

(60) Provisional application No. 61/155,230, filed on Feb. 25, 2009.

(51) Int. Cl.
| | |
|---|---|
| *C12M 3/02* | (2006.01) |
| *B23P 17/04* | (2006.01) |
| *C12M 1/24* | (2006.01) |
| *C12M 1/00* | (2006.01) |
| *C12M 3/00* | (2006.01) |

(52) U.S. Cl.
CPC ............ *C12M 23/08* (2013.01); *C12M 23/34* (2013.01); *C12M 23/40* (2013.01); *C12M 23/44* (2013.01); *Y10T 29/49826* (2015.01)

(58) Field of Classification Search
CPC ...... C12M 23/08; C12M 23/34; C12M 23/40; C12M 23/44; B23K 9/1006; H04W 4/02; Y10T 29/49826
USPC ............ 435/286.6–289.1, 293.1–305.2, 243, 435/286.5, 294.1, 297.1, 297.4, 297.5, 435/298.2, 300.1, 303.1, 303.2, 304.1, 435/304.2, 304.3, 305.1, 297.2, 295.2, 435/299.2, 395; 220/23.83, 4.04; 422/400, 551, 568; 29/428
See application file for complete search history.

(56) References Cited

U.S. PATENT DOCUMENTS

| | | | | |
|---|---|---|---|---|
| 2,865,816 | A | * | 12/1958 | Stefanye et al. ................. 435/39 |
| 4,172,013 | A | | 10/1979 | Skoda et al. |
| 5,693,537 | A | | 12/1997 | Wilson et al. |
| 5,763,267 | A | | 6/1998 | Kurjan et al. .............. 435/293.1 |
| 6,521,129 | B1 | | 2/2003 | Stamper et al. ............... 210/603 |

(Continued)

FOREIGN PATENT DOCUMENTS

| | | | |
|---|---|---|---|
| EP | 0141104 | * | 5/1985 |
| GB | 1539263 | | 1/1979 |
| WO | 2007/015770 | | 2/2007 |

OTHER PUBLICATIONS

Corning CellSTACK Culture Chambers brochure, Corning Incorporated, Printed in USA Jun. 2007.

(Continued)

*Primary Examiner* — Kevin Joyner
*Assistant Examiner* — Holly Mull
(74) *Attorney, Agent, or Firm* — Susan S. Wilks

(57) ABSTRACT

The disclosure provides a cell culture apparatus having multiple stacked cell culture units each having multiple cell culture chambers. The multiple cell culture units are connected by a manifold which connects the cell culture units and provides a mechanism for efficiently filling the multiple cell culture chambers.

22 Claims, 19 Drawing Sheets

(56) References Cited

U.S. PATENT DOCUMENTS

| | | |
|---|---|---|
| 8,809,044 B2 | 8/2014 | Wilson .................. 435/305.2 |
| 2002/0039785 A1* | 4/2002 | Schroeder et al. ........ 435/304.3 |
| 2004/0173285 A1* | 9/2004 | Tawa ........................ 141/324 |
| 2005/0047971 A1 | 3/2005 | Clements et al. ............ 422/102 |
| 2005/0054086 A1* | 3/2005 | Ophardt .................... 435/296.1 |
| 2006/0160206 A1 | 7/2006 | Holmquist et al. ........ 435/287.2 |
| 2007/0026516 A1 | 2/2007 | Martin et al. |
| 2007/0178583 A1* | 8/2007 | Berry ........................ 435/295.2 |
| 2008/0176318 A1 | 7/2008 | Wilson et al. |
| 2008/0206857 A1 | 8/2008 | Kenney et al. |
| 2008/0227176 A1 | 9/2008 | Wilson ........................ 435/243 |
| 2008/0248552 A1* | 10/2008 | Castillo ........................ 435/243 |
| 2008/0299649 A1* | 12/2008 | Martin .................. C12M 23/24 435/297.1 |
| 2009/0298164 A1* | 12/2009 | Cattadoris ........... B29C 45/0053 435/294.1 |

OTHER PUBLICATIONS

Active Gassed Cell Factories Instruction CF4, CF10, og CF40 brochure, Nune, Nov. 2003.
EP13193005.9 Search Report.
Apr. 1, 2014 Translation of Office Action issued by Japanese Patent Office in counterpart Application No. 2011-552141.

* cited by examiner

CELL CULTURE SYSTEM WITH MANIFOLD

CLAIMING BENEFIT OF PRIOR FILED U.S. APPLICATION

This application claims the benefit of U.S. Provisional Application Ser. No. 61/155,230, filed on Feb. 25, 2009. The content of this document and the entire disclosure of publications, patents, and patent documents mentioned herein are incorporated by reference.

FIELD

The present disclosure relates to articles for culturing cells.

BACKGROUND

Many types of cell culture articles are constructed to provide stacked or stackable units for culturing cells. For example, T-flasks are typically made to have flat top and bottom surfaces that allow T-flasks to be stacked, providing space savings. Some modified T-flasks have multiple parallel culture surfaces within the flask to reduce time and effort associated with filling and emptying. Other culture apparatuses are multi-component assemblies having a plurality of parallel or stacked culture surfaces. With most of such stacked culture assemblies, each culture layer is isolated to reduce hydrostatic pressure on the lower culture layers. As the number of stacked layers increases, the potential effect of hydrostatic pressure increases.

Some cell culture articles are designed to operate with minimal or no headspace. For example, Corning's HYPERFlask™ is often filled nearly completely for proper culture conditions. The HYPERFlask™ contains ten cell culture chambers with 172 $cm^2$ culture surfaces in the space and general shape of a traditional 175 $cm^2$ flask. In such a system, the lower chambers are subjected to increased hydrostatic pressure relative to the upper chambers. Increasing the number of cell culture chambers in such a system with limited or no headspace would further increase hydrostatic pressure in the lower cell culture chambers, which may be undesirable. However, it may be desirable from an efficiency perspective, in terms of time and space, to increase the number of cell culture layers in such systems.

BRIEF SUMMARY

The present disclosure describes, among other things, in embodiments, a multilayered cell culture apparatus having layers of cell culture chambers connected via manifolds that allow the layers of cell culture chambers to be filled, in series or in parallel. The manifolds also allow for air, displaced from the filling cell culture chambers, to exit the cell apparatus. In addition, manifolds, configured according to embodiments of the present invention, allow for the creation of an air gap between layers of cell culture chambers, or groups of layers of cell culture chambers (cell culture units). This air gap reduces the hydrostatic pressure on multiple layers of liquid-filled cell culture chambers.

In various embodiments, the disclosure describes a cell culture apparatus having at least two cell culture units, each having a top surface and each containing at least two cell culture chambers; manifolds connecting each of the at least two culture units with a fluid flow channel, allowing a fluid connection between the fluid flow channel and the culture chambers; wherein at least one manifold connected to a cell culture unit has a dam which extends above the top surface of the connected cell culture unit when the cell culture unit is positioned for cell culture. In embodiments, the cell culture apparatus has a liquid fluid flow channel for liquid flow into the cell culture unit. In embodiments the cell culture apparatus has an exhaust fluid flow channel for allowing displaced air to exit the apparatus. In embodiments, the cell culture apparatus has both a liquid fluid flow channel and an exhaust fluid flow channel. In embodiments, one manifold connected to a liquid fluid flow channel does not have a dam. In embodiments, the liquid fluid flow channel has a valve. In embodiments, the manifold has a reservoir structured and arranged to provide an air space between the cell culture unit and the fluid flow channel when the cell culture apparatus is positioned for cell culture. In embodiments, at least two cell culture units are connected to each other in parallel through a fluid flow channel. In additional embodiments, at lest two cell culture units are connected to each other in series through a fluid flow channel.

In additional embodiments, the disclosure describes a cell culture apparatus, having at least two cell culture units, each having at least two culture chambers and a filling port having an inlet, an overflow outlet, and a cell culture outlet in fluid communication with the at least two culture chambers to allow fluid introduced through the inlet to enter the chambers through the cell culture outlet, wherein the filling port is configured to cause fluid introduced into the inlet to flow out the overflow outlet when the culture chambers are filled with fluid.

In embodiments, the at least two cell culture units also have a second filling port having an inlet, an overflow outlet and a cell culture outlet in fluid communication with the at least two culture chambers to allow fluid introduced through the inlet of the second filling port to enter the cell culture chambers of the cell culture unit through the cell culture outlet of the second filling port. In embodiments, the overflow outlet of a first cell culture unit is fluidly coupled to the inlet of a second cell culture unit. In embodiments, the overflow outlets of the first and second filling ports of a first cell culture unit are fluidly coupled to the inlets of a first and second overflow ports of a second cell culture unit. In embodiments, one cell culture unit is stacked above and fluidly coupled to a second cell culture unit. In embodiments, multiple cell culture units are stacked one above another, and are fluidly coupled to each neighboring cell culture units.

In embodiments, the cell culture apparatus includes a filling port and at least two cell culture units having at least two cell culture chambers. In embodiments, the filling port has an inlet, an overflow outlet, and a cell culture outlet. The cell culture outlet is in fluid communication with the culture chamber to allow fluid introduced through the inlet to enter the chamber through the cell culture outlet. The filling port is configured to cause fluid introduced into the inlet to flow out the overflow outlet when the culture chamber is filled with fluid. The filling port may be coupled to other ports in a manifold, such that when the fluid flows out of the overflow outlet it can flow into an inlet of a port below, which can then serve to fill another cell culture chamber to which the lower port is in communication.

In embodiments, the manifolds have a filling port which has an inlet in fluid communication with at least one cell culture chamber. In embodiments, the filling port has a reservoir structured and arranged to provide an air space in the port when the cell culture apparatus is in a cell culture position. In embodiments, the at least one cell culture chamber is connected to another cell culture chamber through the fluid flow channel. In embodiments, the cell culture apparatus has an air outlet in fluid communication with the culture chamber to allow displaced air to leave the chamber. In embodiments, at least two culture chambers are connected to each other in parallel through the air outlet. In embodiments, the at least two culture chambers are connected to each other in parallel through the fluid flow channel. In additional embodiments, the at least two cell culture chambers are connected to each other in parallel through the fluid flow channel and through the air outlet. In additional embodiments, the at least cell culture units are connected to each other in series through a fluid flow channel.

In embodiments, the disclosure provides cell culture articles that are assembled together to form a multi-layer stack of culture chambers. In embodiments, individual chambers or groups of chambers are connected to each other via one or more manifolds. In embodiments, the manifolds allow filling of the individual chambers or groups of chambers from the uppermost position sequentially to the lowermost position via a cascading effect. In embodiments, manifolds are configured to allow isolation of the individual chambers or groups of chambers to prevent excessive hydrostatic pressure on the lower chambers or groups of chambers.

In various embodiments, the disclosure describes a cell culture apparatus including a cell culture unit and a filling port. The cell culture unit has a culture chamber having a top surface and a bottom surface. The filling port has an inlet, a culture outlet, an overflow outlet, a first passageway, and a second passageway. The inlet, the first culture outlet, and the overflow outlet are in fluid communication. The first culture outlet is in fluid communication with the chamber of the culture unit. The first passageway provides fluid communication between the inlet and the first outlet. The second passageway is between the inlet and the overflow outlet and is in fluid communication with the first passageway. At least a portion of the second passageway has a cross-section where the entire cross-section is above the top surface of the cell culture chamber when the bottom surface of the cell culture chamber is below the top surface of the chamber.

In various embodiments, a method for manufacturing a cell culture article is described. The method includes (i) providing a first cell culture unit having a first cell culture chamber and an opening; (ii) providing a first filling port having an inlet, a cell culture outlet, and an overflow outlet, wherein the inlet, the cell culture outlet and the overflow outlet are in fluid communication; (iii) providing a second cell culture unit having a cell culture chamber and an opening; and (iv) providing a second filling port having an inlet, a cell culture outlet, and an overflow outlet, wherein the inlet, the cell culture outlet and the overflow outlet are in fluid communication. The method further includes coupling the first port to the first culture unit such that (i) the cell culture outlet of the first filling port is fluidly coupled to the opening of the first cell culture unit to allow fluid introduced into the inlet of the first port to enter the chamber of the first culture unit, and (ii) the first filling port is oriented to cause fluid poured into the inlet of the first port to flow out the overflow outlet of the first port when the culture chamber is filled with fluid. The method further includes coupling the second port to the second culture unit such that (i) the cell culture outlet of the second filling port is fluidly coupled to the opening of the second cell culture unit to allow fluid introduced into the inlet of the second port to enter the chamber of the second culture unit, and (ii) the second filling port is oriented to cause fluid poured into the inlet of the second port to flow out the overflow outlet of the second port when the culture chamber of the second culture unit is filled with fluid. The method also includes stacking the first cell culture unit above the second cell culture unit, and fluidly coupling the inlet of the second filling port to the overflow outlet of the first port.

Culture apparatuses described herein may be stacked into multi-layer culture chamber assemblies where individual chambers or groups of chambers are connected to each other via one or more manifolds and where each chamber or groups of chambers are isolated with regard to headspace to avoid excessive hydrostatic pressure on the lower chambers or groups of chambers. This and other advantages will be readily understood from the following detailed descriptions when read in conjunction with the accompanying drawings.

Figure 1:
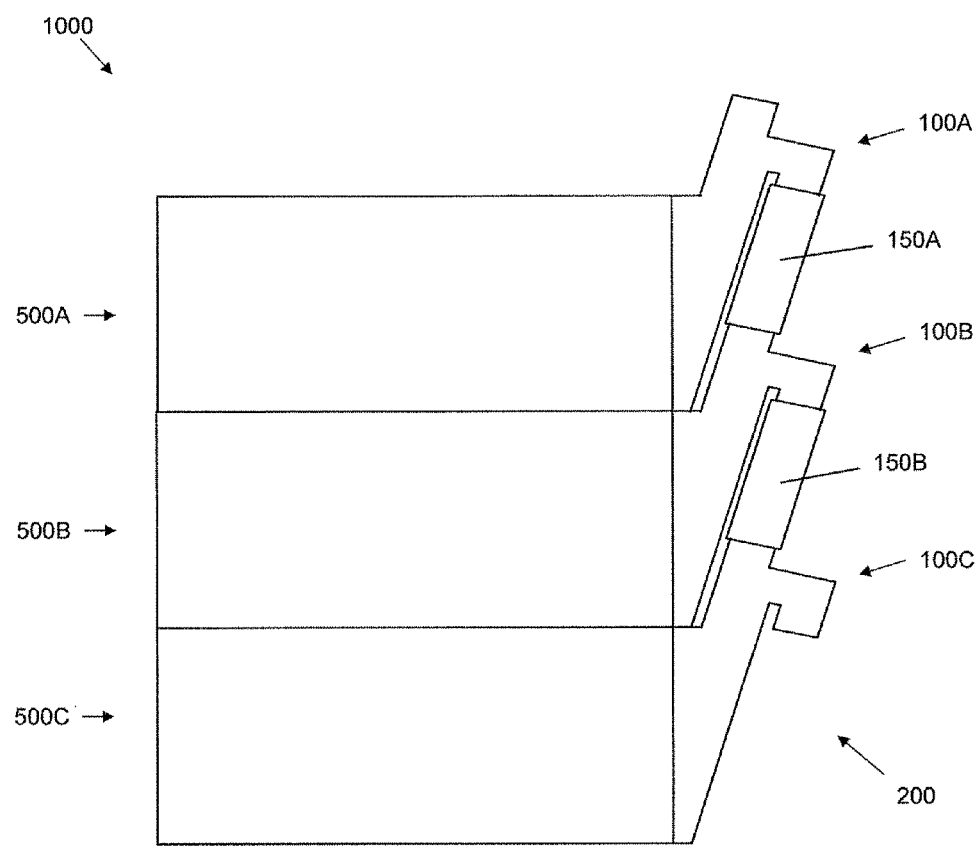
FIG. 1 is a schematic side view of a cell culture apparatus including a manifold coupled to a plurality of cell culture units.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The present disclosure describes, inter alia, cell culture articles having a plurality of growth or culture surfaces in cell culture chambers coupled together via manifolds to form cell culture units. The cell culture units can be further coupled to additional cell culture units via manifolds to form stacked cell culture articles. The plurality of culture surfaces may be stacked in a multi-layer configuration. The manifold includes a plurality of fluidly coupled ports that serve to provide fluid flow to individual or groups of cell culture chambers. In embodiments, the manifold is configured to allow filling of the individual or groups of cell culture chambers from the uppermost chamber or group of chambers sequentially, in series, to the lowermost chamber or group of chambers via a cascading effect. In additional embodiments, the manifold is configured to allow filling of the individual or groups of cell culture units or cell culture chambers simultaneously, or in parallel. The ports of the manifold are configured to avoid formation of a fluid column in the manifold between the ports for filling the individual or groups of chambers, which reduces or eliminates excessive hydrostatic pressure in the lowermost culture chambers.

Nearly any cell culture article having a plurality of stacked layers or that can be stacked to form layers can be adapted to include a manifold as described herein. Examples of such cell culture articles include T-flasks, TRIPLE-FLASK cell culture vessels (Nunc., Intl.), HYPERFlask-™cell culture vessels (Corning, Inc.), CellSTACK™ culture chambers (Corning, Inc.), CellCube® modules (Corning, Inc.), CELL FACTORY culture apparatuses (Nunc, Intl.), and cell culture articles as described in WO 2007/015770, entitled "MULTILAYERED CELL CULTURE APPARATUS", and published Feb. 8, 2007, which publication is hereby incorporated by reference in its entirety to the extent that it does not conflict with the disclosure presented herein.

Referring to FIG. 1, a schematic side view of a cell culture apparatus 1000 including a manifold 200 coupled to a plurality of cell culture units 500A, 500B, 500C is shown. The depicted manifold 200 includes a plurality of ports 100A, 100B, 100C. Each port 100A, 100B, 100C of the manifold 200 is fluidly coupled to a cell culture unit 500A, 500B, 500C. Each cell culture unit 500A, 500B, 500C may individually contain one of more cell culture chambers. The ports 100A, 100B, 100C depicted in FIG. 1 are fluidly coupled 150A, 150B. The ports may be fluidly coupled via tubing, or by any other connector.

Figure 2:
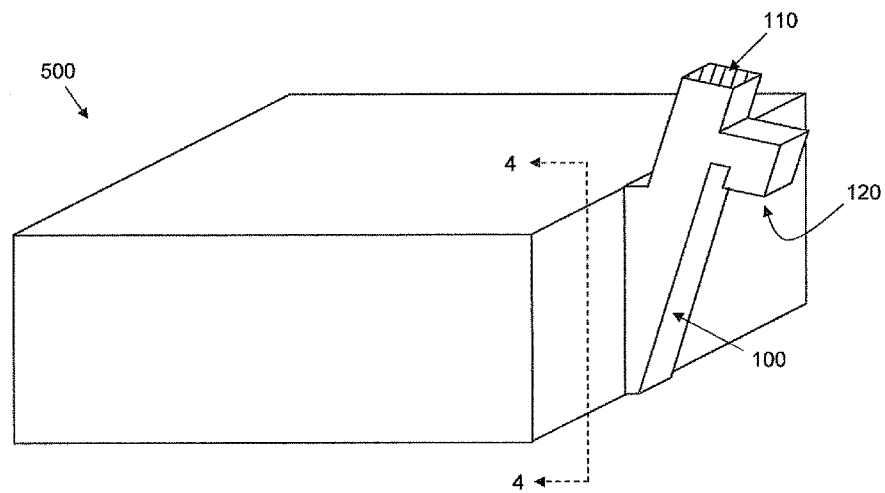
FIGS. 2-3 are schematic perspective views of embodiments of a cell culture unit and associated filling port(s).
Figure 3:
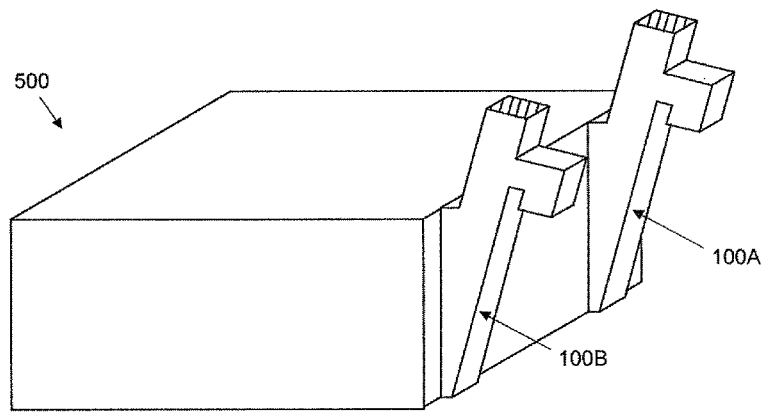

Referring now to FIGS. 2-3, schematic perspective views of a cell culture unit 500 and associated filling port(s) 100(A,B) are shown. As shown, one port 100 (FIG. 2) or more than one port 100A, 100B (FIG. 3) may be coupled to a cell culture unit 500. Filling port 100 includes an inlet 110 and an overflow outlet 120, which will be discussed in greater detail below.

Figure 4A:
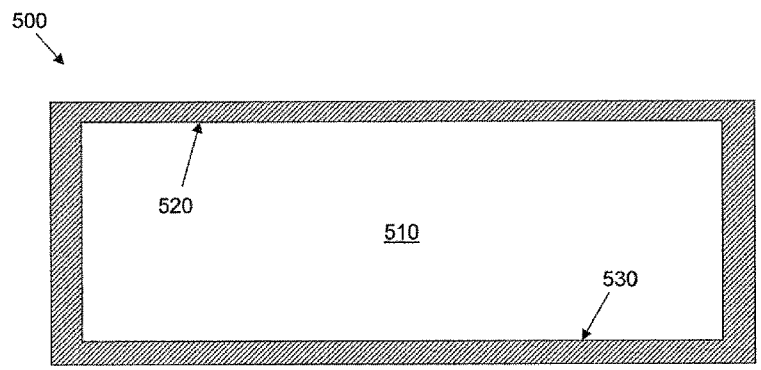
FIGS. 4A-B are schematic cross-sections of embodiments of the cell culture unit depicted in FIG. 2.
Figure 4B:
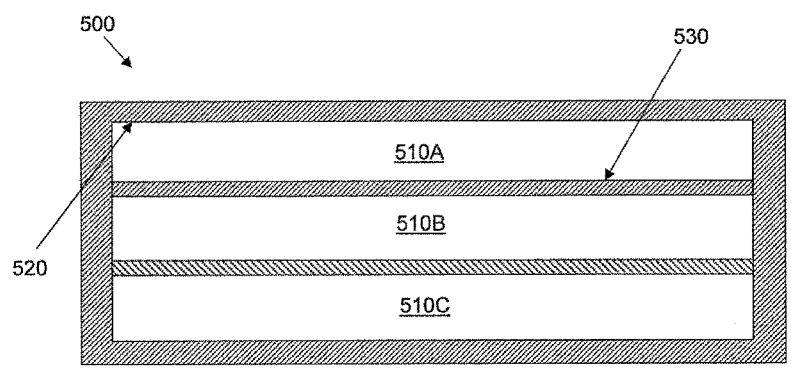

FIGS. 4A-B are schematic cross-sections of embodiments of the cell culture unit 500 depicted in FIG. 2. The sections shown in FIGS. 4A-B are taken through line 4-4 of FIG. 2. In FIG. 4A, the depicted cell culture unit 500 has one cell culture chamber 510 having a top surface 520 and a bottom surface 530. For purposes of culturing cells, the depicted cell culture unit 500 is typically oriented such that the top surface 520 of the chamber 510 is above the bottom surface 530, so cells may be cultured on the bottom surface 530. In the embodiment, depicted in FIG. 4B, the cell culture unit 500 contains more than one chamber 510A, 510B, 510C in which cells may be cultured. Each chamber has a bottom 530 surface and a top surface 520.

Figure 5:
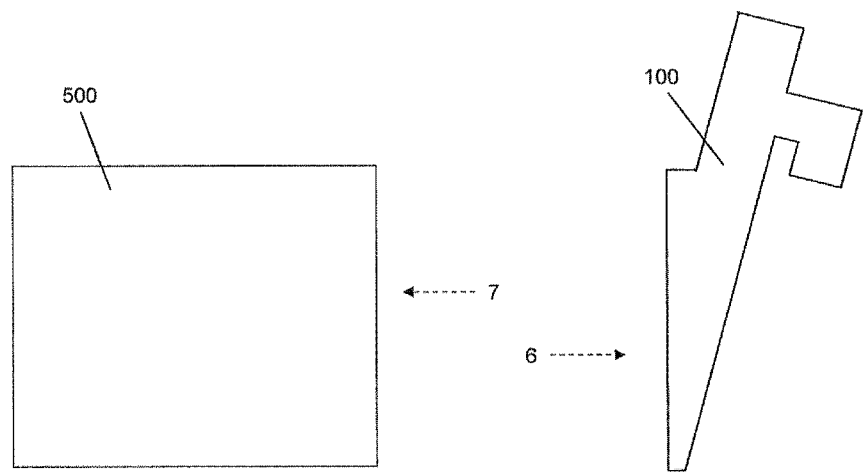
FIG. 5 is a schematic exploded side view showing a cell culture unit and a filling port.
Figures 6A, 6B:
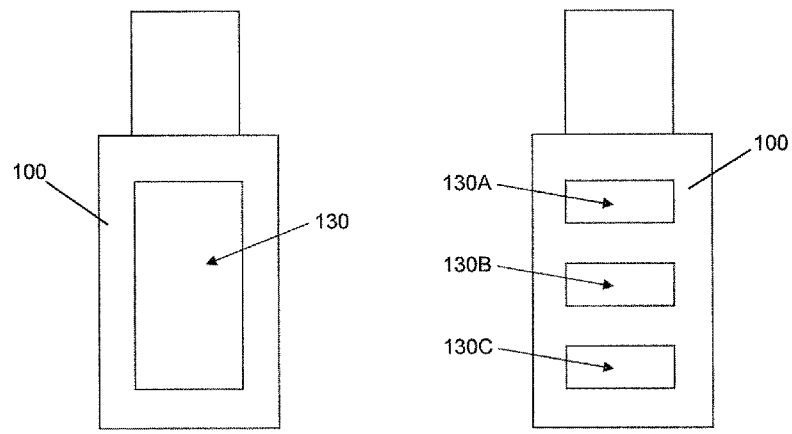
FIGS. 6A-B are head-on front views of alternative embodiments of the filling port viewed along line 6 in FIG. 5.

Referring now to FIGS. 5-7, various embodiments of a cell culture unit 500 and associated filling port 100 are shown. FIG. 5 is a schematic exploded side view showing a cell culture unit 500 and a filling port 100. In various embodiments, a cell culture unit 500 and a filling port 100 are formed separately and joined during manufacture or assembly of the cell culture apparatus. FIGS. 6A-B are head-on front views of alternative embodiments of the filling port 100 viewed along line 6 in FIG. 5. In FIG. 6A, the filling port has one culture outlet 130, and in FIG. 6B the filling port 100 has more than one culture outlet 130A, 130B, 130C.

Figure 7A:
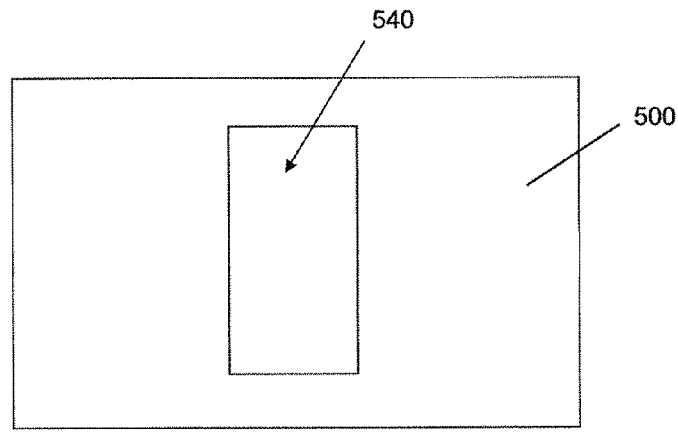
FIGS. 7A-B are head-on from views of alternative embodiments of the cell culture unit viewed along line 7 in FIG. 5.
Figure 7B:
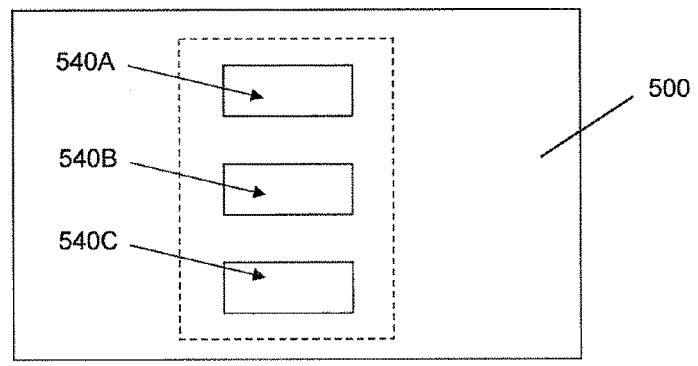

FIGS. 7A-B are head-on from views of alternative embodiments of the cell culture unit 500 viewed along line 7 in FIG. 5. In FIG. 7A, the cell culture unit 500 has one opening 540 in fluid communication with the cell culture chamber defined by the unit (e.g., a cell culture unit 500 as shown in the schematic cross section of FIG. 4A). In FIG. 7B, the cell culture unit 500 has more than one opening 540A, 540B, 540C. Each opening 540A, MOB, 540C may be in fluid communication with an individual cell culture chamber of the unit 500 (e.g., cell culture chambers 510A, 510B, 510C as shown in FIG. 4B).

In various embodiments, the cell culture outlet(s) 130 of a filling port 100 are shaped and sized to be substantially the same shape and size as the opening(s) 540 of a cell culture unit 500. By way of example, a filling port 100 as shown in FIG. 6A having one culture outlet 130 may be coupled with a culture unit 500 as shown in FIG. 7A having one opening 540. Similarly, a filling port 100 as shown in FIG. 6B having three culture outlets 130A, 130B, 130C may be coupled with a culture unit 500 as shown in FIG. 7A having three openings 540A, 540B, 540C. Alternatively, a port 100 as shown in FIG. 6A may be coupled with a culture unit 500 as shown in FIG. 7B such that when coupled, three cell culture outlets are effectively formed. For example, if a port 100 as depicted in FIG. 6A is fluidly sealed to a cell culture unit 500 as depicted in FIG. 7B in the area around the openings 540A, 540B, 540C (as indicated by the dashed rectangular box), three culture outlets are effectively formed, each being in communication with an individual culture chamber if each of the openings 540A, 540B, 540C are in communication with individual culture chambers of the unit (e.g., if the unit 500 has a cross-sectional configuration as shown in, for example, FIG. 4B).

Figure 8:
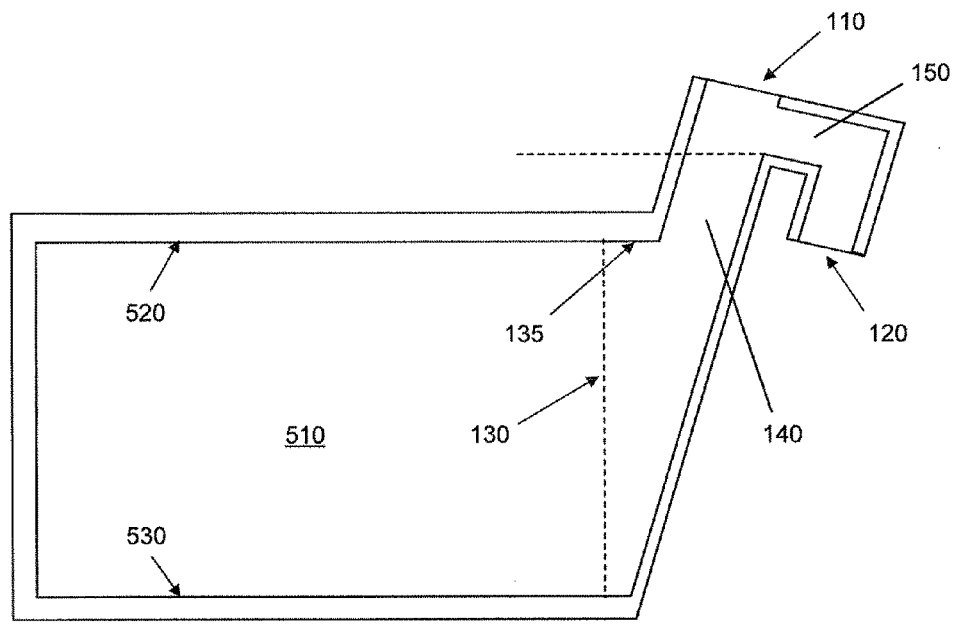
FIG. 8 is a schematic cross-section of a filling port and associated cell culture unit is shown.

Referring now to FIG. 8, a schematic cross-section of a filling port and associated cell culture unit is shown. A dashed line is shown to indicate an imaginary line between the filling port and the cell culture unit. The filling port has an inlet 110, an overflow outlet 120, and a cell culture outlet 130. The inlet 110, the overflow outlet 120 and the culture outlet 130 are in fluid communication. As described above, a port may contain more than one cell culture outlet and the cell culture outlet(s) is(are) in fluid communication with a cell culture chamber(s) when the port is coupled to a cell culture unit. The port 100 is configured to cause fluid introduced into the inlet 110 to flow into a cell culture chamber via the culture outlet 130, and when the culture chamber is filled with fluid, to cause the fluid introduced into the inlet 110 to flow out the overflow outlet 120.

The filling port depicted in FIG. 8 has a first passageway 140 providing fluid communication between the inlet 110 and the culture outlet 130. The port also includes a second passageway 150 between the inlet 110 and the overflow outlet 120. The second passageway 150 is in fluid communication with the first passageway 140. At least a portion (indicated by upper dashed line) of the entire cross-section of the second passageway 150 is above the top surface 520 of the cell culture chamber 510 (when the top surface 520 is above the bottom surface 530; e.g., when the top surface 520 is oriented up and the bottom surface 530 is oriented down). In the depicted embodiment, the topmost portion 135 of the cell culture outlet 130 is below the level of the portion (indicated by upper dashed line) the second passageway 150. By having at least a portion of the second passageway 150 above the top surface of the chamber 510, the chamber 510 may be filled with fluid before additional fluid introduced through the inlet 110 flows through the overflow outlet 120. In embodiments, the overflow outlet 120 is separated from the first passageway by a dam 160. In embodiments, the dam 160 extends above the top surface 520 of the chamber to allow liquid to fill the chamber, and partially fill the first passageway, but to allow an air pocket to reside in the second passageway 150 when the apparatus is in use in cell culture.

Figure 9A:
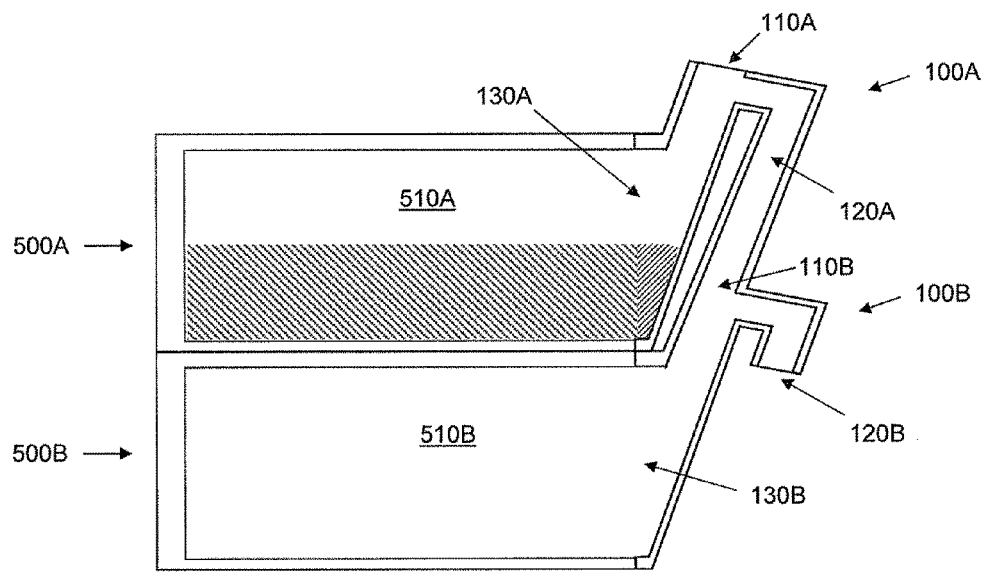
FIGS. 9A-C are schematic cross-sectional views of an apparatus including two cell culture units and a manifold with two filling port components.
Figure 9B:
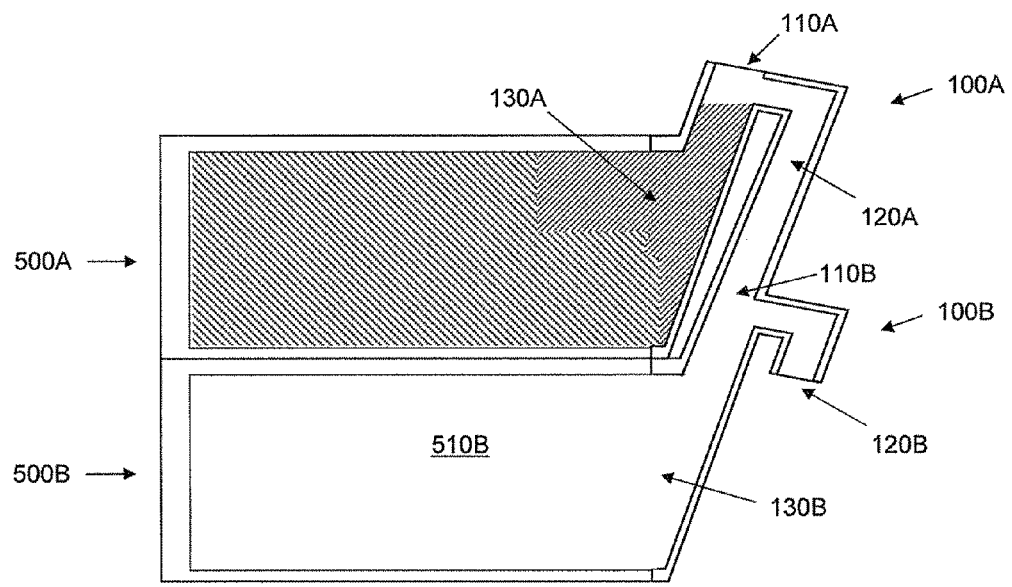
Figure 9C:
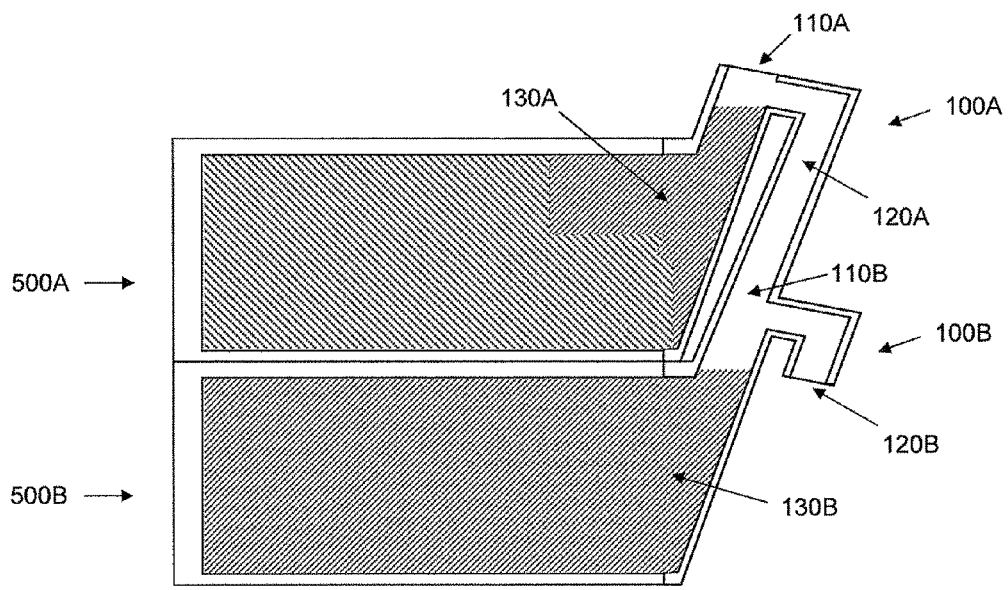

Referring now to FIGS. 9A-C, schematic cross-sectional views of an apparatus including two cell culture units 500A, 500B and a manifold with two filling port components are shown. The chamber 510A of the upper cell culture unit 500A in FIG. 9A is shown partially filled with cell culture media (indicated by hatched area). The addition of more media fills the upper chamber 510 and a portion of the first passageway of the port 100A (see FIG. 9B). As shown in FIG. 9B, the upper culture chamber is filled with media and the first passageway is filled to a level to which introduction of any additional cell culture media into the inlet 110A will cause the media to flow out of the overflow outlet 120A over dam 160A of the first port region 100A and into the inlet 110B of the second port region 100B positioned below the first port region 110B. In the embodiment depicted in FIG. 9, the overflow outlet 120A of the upper filling port 110A of the manifold is continuous with the inlet 110B of the lower filling port 100B. In some embodiments, the overflow outlet of the upper port is coupled to the inlet of the lower port via tubing (see, e.g., FIG. 1) or otherwise.

Adding additional media to the manifold inlet 110A depicted in FIG. 9B, will cause media to flow out of outlet 120A over dam 160A, and into the lower port inlet 110B to begin filling the lower chamber 510B. Once the lower chamber 510B is full (see FIG. 9C) and the addition of more media is stopped, an air gap exists in the manifold between the upper and lower culture chambers because of dam 160A, isolating the chambers and avoiding increased hydrostatic pressure in the lower chamber. If additional media is added to inlet 110A, the media will exit the overflow outlet 120B over dam 160B of the lower portion 100B of the manifold to maintain the air gap. If additional cell culture units and associated ports of the manifold are positioned below the lower unit 500B and if more media is added, the chambers of the additional units can be filled sequentially from highest to lowest.

A cell culture unit, or portions thereof, as described herein may be formed from any suitable material. Preferably, materials intended to contact cells or culture media are compatible with the cells and the media. Typically, cell culture units are formed from polymeric material. Examples of suitable polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

In some embodiments, the culture units contain a gas permeable, liquid impermeable film to allow transfer of gasses between a cell culture chamber and the exterior of the cell culture assembly. Such culture units can include spacers or spacer layers positioned adjacent the film, exterior to the chamber, to allow air flow between stacked units. One commercially available example of a cell culture apparatus containing such stacked gas permeable culture units is Corning's HYPERFlask™ cell culture apparatus. Such cell culture units may be manufactured in any suitable manner, such as, for example, U.S. Patent Application Ser. No. 61/130,421, entitled Assembly of Cell Culture Vessels, filed on May, 30, 2008, which application is hereby incorporated herein by reference in its entirety to the extent it does not conflict with the disclosure presented herein. Examples of suitable gas permeable polymeric materials useful for forming a film include polystyrene, polyethylene, polycarbonate, polyolefin, ethylene vinyl acetate, polymethylpentene, polypropylene, polysulfone, polytetrafluoroethylene (PTFE), or compatible fluoropolymer, a silicone rubber or copolymer, poly(styrene-butadiene-styrene) or combinations of these materials. As manufacturing and compatibility for the growth of cells permits, various polymeric materials may be utilized. Preferably the film is of a thickness that allows for efficient transfer of gas across the film. For example, a polystyrene film may be of a thickness of about 0.003 inches (about 75 micrometers) in thickness, though various thicknesses are also permissive of cell growth. As such, the membrane may be of any thickness, preferably between about 25 and 250 micrometers, or between approximately 25 and 125 micrometers. The membrane allows for the free exchange of gases between the chamber of the assembly and the external environment and may take any size or shape. Preferably, the membrane is durable for manufacture, handling, and manipulation of the apparatus.

Figure 10A:
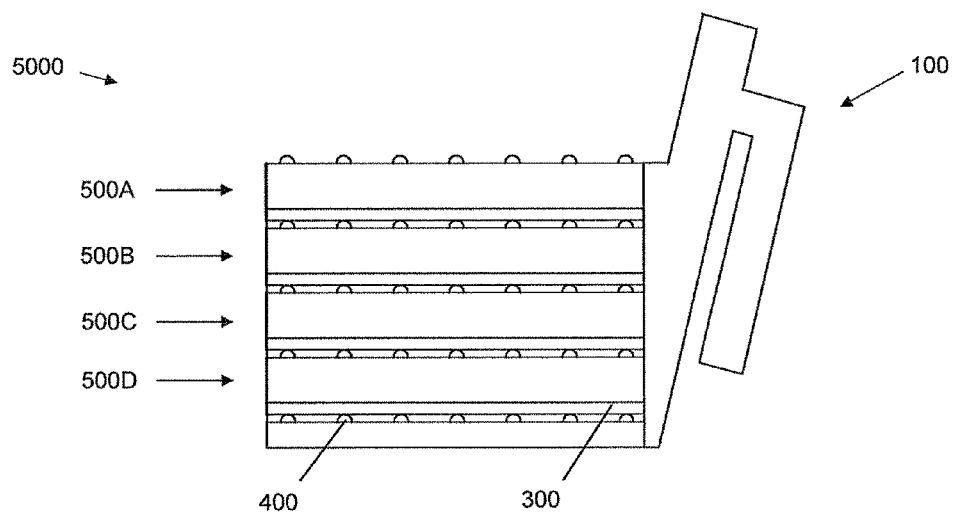
FIG. 10A is a schematic side view of a cell culture article that includes a plurality of cell culture units operably coupled to a filling port.
Figure 10B:
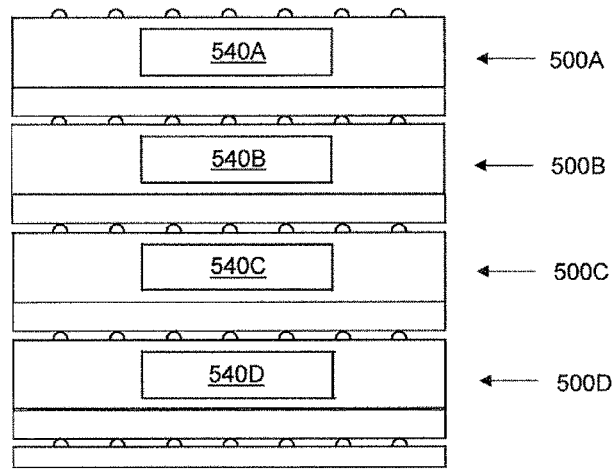
FIG. 10B is a schematic head-on front view of an embodiment of the cell culture units depicted in FIG. 10A.
Figure 10C:
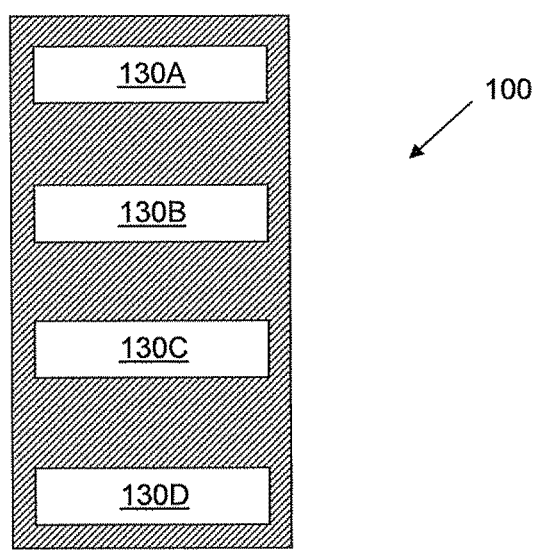
FIG. 10C is s schematic head-on from view of an embodiment of a portion of the filling port depicted in FIG. 10A.

Referring to FIGS. 10A-C, various schematic views of an embodiment of a cell culture article 5000 or portions thereof are shown. In the schematic side view shown in FIG. 10A, the article 5000 includes a plurality of cell culture units 500A, 500B, 500C, 500D operably coupled to a filling port 100. Each of the depicted cell culture units 500A, 500B, 500C, 500D include a gas permeable film 300 that forms at least a portion of a cell culture chamber and allows gas to transfer between the chamber and the exterior of the apparatus. Spacers 400 are positioned adjacent the gas permeable film 300, exterior to the chamber, to provide a passageway for air flow.

FIG. 10B is a schematic head-on front view of an embodiment of the cell culture units 500A, 500B, 500C, 500D depicted in FIG. 10A. Each of the culture units 500A, 500B, 500C, 500D has an opening 540A, 540B, 540C, 540D in fluid communication with a cell culture chamber.

FIG. 10C is s schematic head-on from view of an embodiment of a portion of the filling port 100 depicted in FIG. 10A. The portion of the port 100 shown in FIG. 10C is the portion of the port 100 that contacts the cell culture units 500A, 500B, 500C, 500D depicted in FIG. 10A. As shown in the embodiment depicted in FIG. 10C, the port 100 includes four culture outlets 130A, 130B, 130C, 130D. When the filling port 100 is coupled to the culture units 500A, 500B, 500C, 500D, the culture outlets 130A, 130B, 130C, 130D are fluidly coupled to the openings 540A, 540B, 540C, 540D (see FIG. 10B) and thus are in fluid communication with the cell culture chambers.

Figure 11:
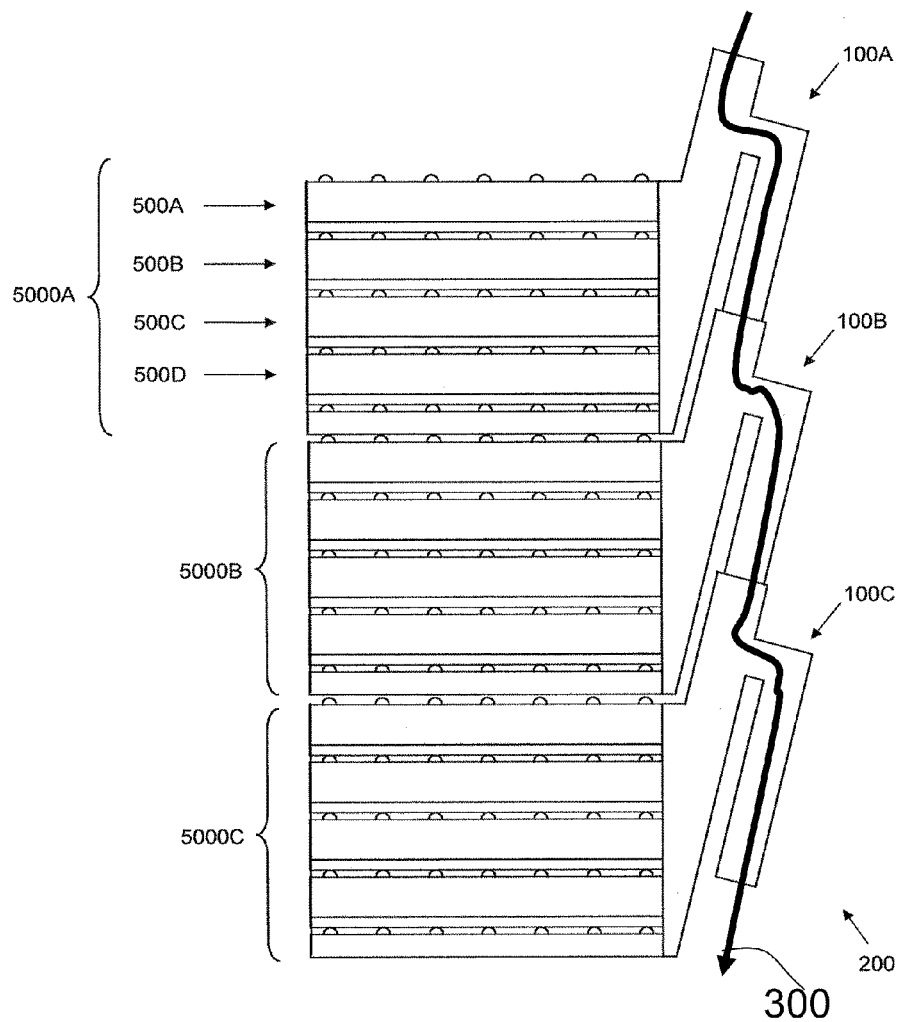
FIG. 11 is a schematic side view of a cell culture article including stacked culture modules.

Referring now to FIG. 11, a schematic side view of a cell culture article including stacked culture modules 5000A, 5000B, 5000C is shown. The modules 5000A, 5000B, 5000C may be a cell culture article 5000 as described above with regard to FIGS. 10A-C. The modules 5000A, 5000B, 5000C include a plurality of cell culture units 500A, 500B, 500C, 500D and an associated filling port 100A, 100B, 100C. The modules 5000A, 5000B, 5000C may be stacked and the ports 100A, 100B, 100C of the manifold operably coupled (e.g., coupling an overflow outlet of a port to the inlet of the port below). The coupled manifold, the coupling of an overflow outlet of a port to the inlet of a port below, forms a fluid flow channel 300. In this embodiment, the stacked cell culture units are coupled in series via the fluid flow channel. That is, liquid is added to the top cell culture unit, the unit fills and the fluid flows through the overflow port to the filling port of the cell culture unit below, the second unit fills and the fluid flows through the overflow port to the filling port of the cell culture unit below, and so on, filling the cell culture units from the topmost unit to the bottommost unit in series. The ports may be coupled via any suitable mechanism. While fluid added to the top cell culture unit may also fill the cell culture chambers, for the purposes of this description, in this embodiment, the fluid flow channel is considered to be as shown by the arrow in FIG. 11. For example, interference fit or compression fit (e.g., including O-ring or barb) may be used to connect the ports. Alternatively or in addition, the ports may be welded, e.g., via sonic or laser welding, held together by adhesive, or the like.

Stacked cell culture articles or units or modules as described herein, may be held together via a manifold, via adhesive, via a fastener such as a rivet, via a weld, or the like.

In various embodiments, a manifold as described herein may be assembled and then attached to stacked cell culture units. In some embodiments, the manifold is molded as one piece and then attached to the stacked cell culture articles (e.g., see FIG. 9). In other embodiments, the ports of the manifolds are formed, e.g., via molding, and then assembled into the manifold. The ports of a manifold may be formed from a single part (see, e.g., FIGS. 10-11) or may be formed from multiple parts.

Figure 12A:
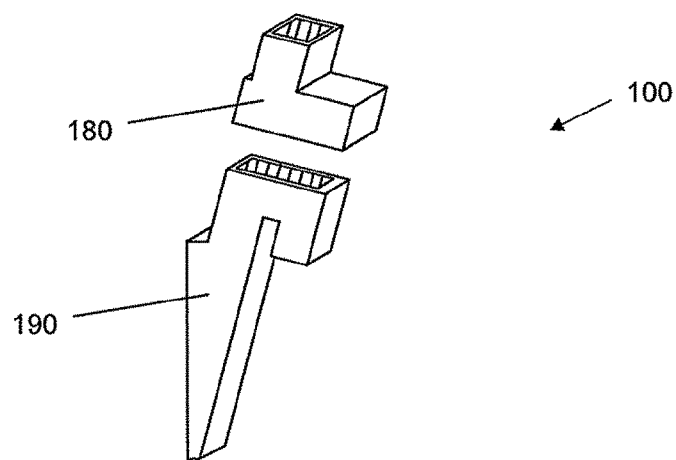
FIG. 12A is a schematic perspective view of parts of a multipart port.
Figure 12B:
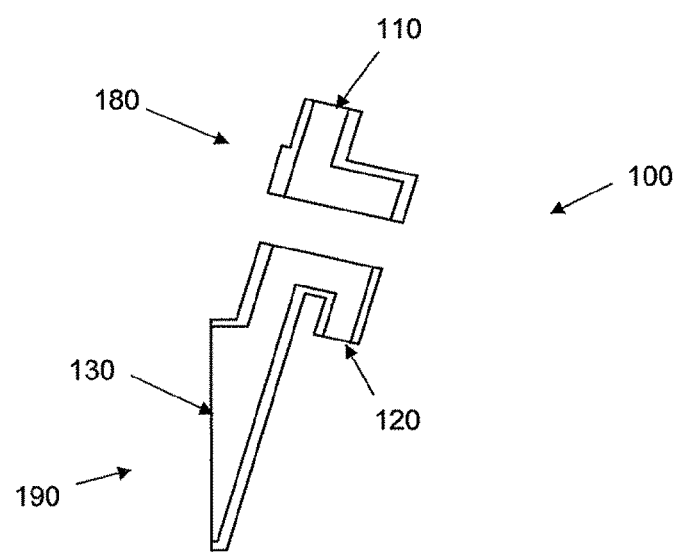
FIG. 12B is schematic cross-sectional view of an embodiment of the multi-part port depicted in FIG. 12A.

For example and referring to FIGS. 12A-B, schematic views of a multi-part port 100 are shown. The port 100 includes a cap portion 180 and a base portion 190. When placed together, the cap 180 and base 190 form a port 100 having an inlet 110, dam 160, an overflow outlet 120, and a culture outlet 130, e.g. as described above. The cap 180 and the base 190 may be formed of the same or different materials. The cap 180 and base 190 may be held together by interference fit, compression fit, adhesive, a weld, or the like. While the multi-part port depicted in FIGS. 12A-B contains two parts, it will be understood that a port as described herein may be made from any number of parts.

Figure 13:
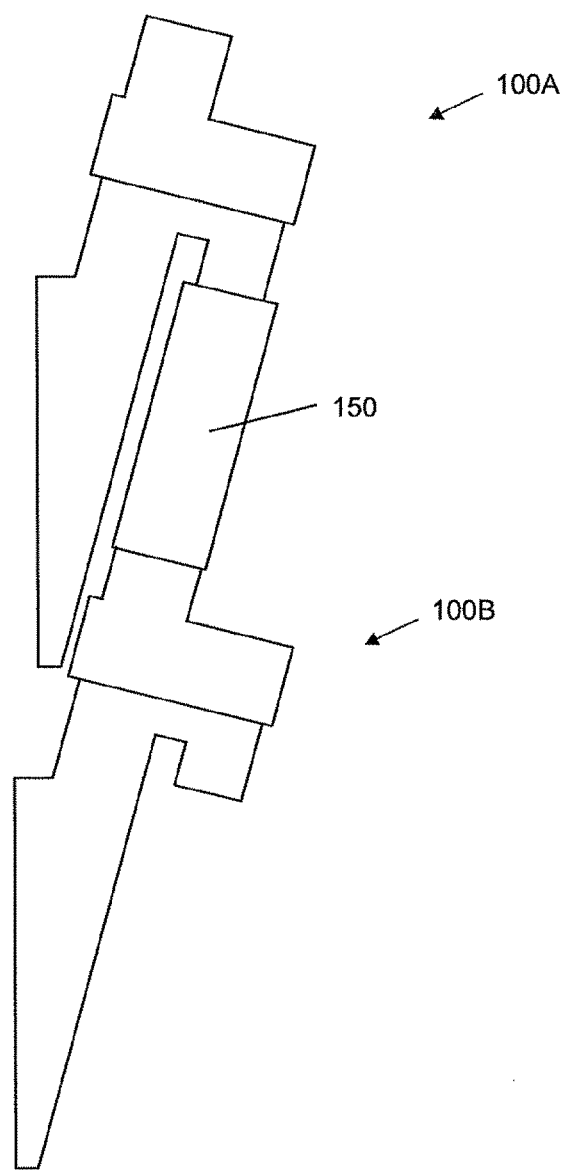
FIG. 13 is a schematic side view of two ports joined by tubing.

Referring now to FIG. 13, two ports 100A, 100B are shown joined by a section of tubing 150. The tubing 150 may be joined to the ports 100A, 100B by any suitable mechanism, such as compression fit, interference fit, adhesive, weld, or the like. The tubing may be formed from any suitable material. In various embodiments the tubing is formed from a flexible material such as silicone or a thermoplastic elastomer.

Figure 14:
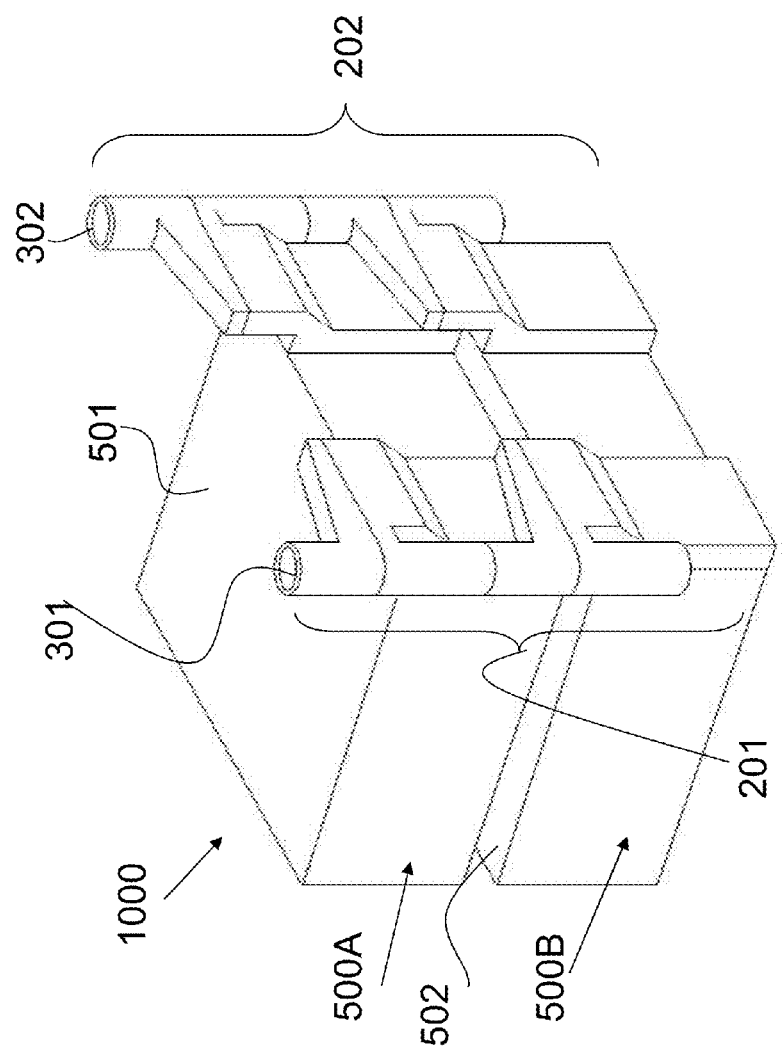
FIG. 14 is a perspective view of an embodiment of the cell culture apparatus.

FIG. 14 is a perspective view of an embodiment of the cell culture apparatus showing two stacked culture units 500A and 500B (although the apparatus may have more than two culture units), each having a top surface (501 and 502), and an additional embodiment of the manifold 200. In this embodiment, liquid entering the cell culture apparatus enters through a liquid fluid flow channel 301 of one manifold 201, while air escapes through a gas exhaust channel 302 of a second manifold 202. The liquid fluid flow channel allows liquid flow into the cell culture unit. The exhaust fluid flow channel allows displaced air to exit the apparatus. The manifolds connect each of the culture units 500A and 500B with fluid flow channels 301 and 302, allowing a fluid connection between the fluid flow channels and the cell culture units. Proteinaceous fluids such as cell culture medium have a propensity for foaming if air is forced through the medium, or the medium experiences turbulence. Having a separate pathway for air to exit the vessel as it is displaced by fluid reduces the occurrence of foam formation.

Figure 15:
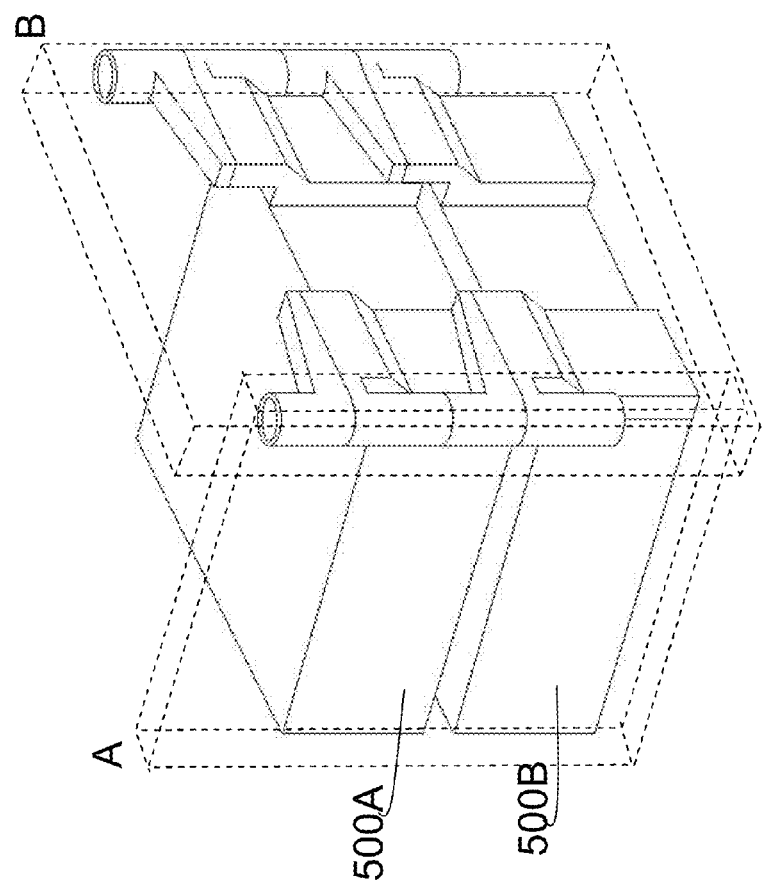
FIG. 15 is a perspective view of the embodiments shown in FIG. 14, illustrating the cross-sections that are shown in FIG. 16.
Figure 16:
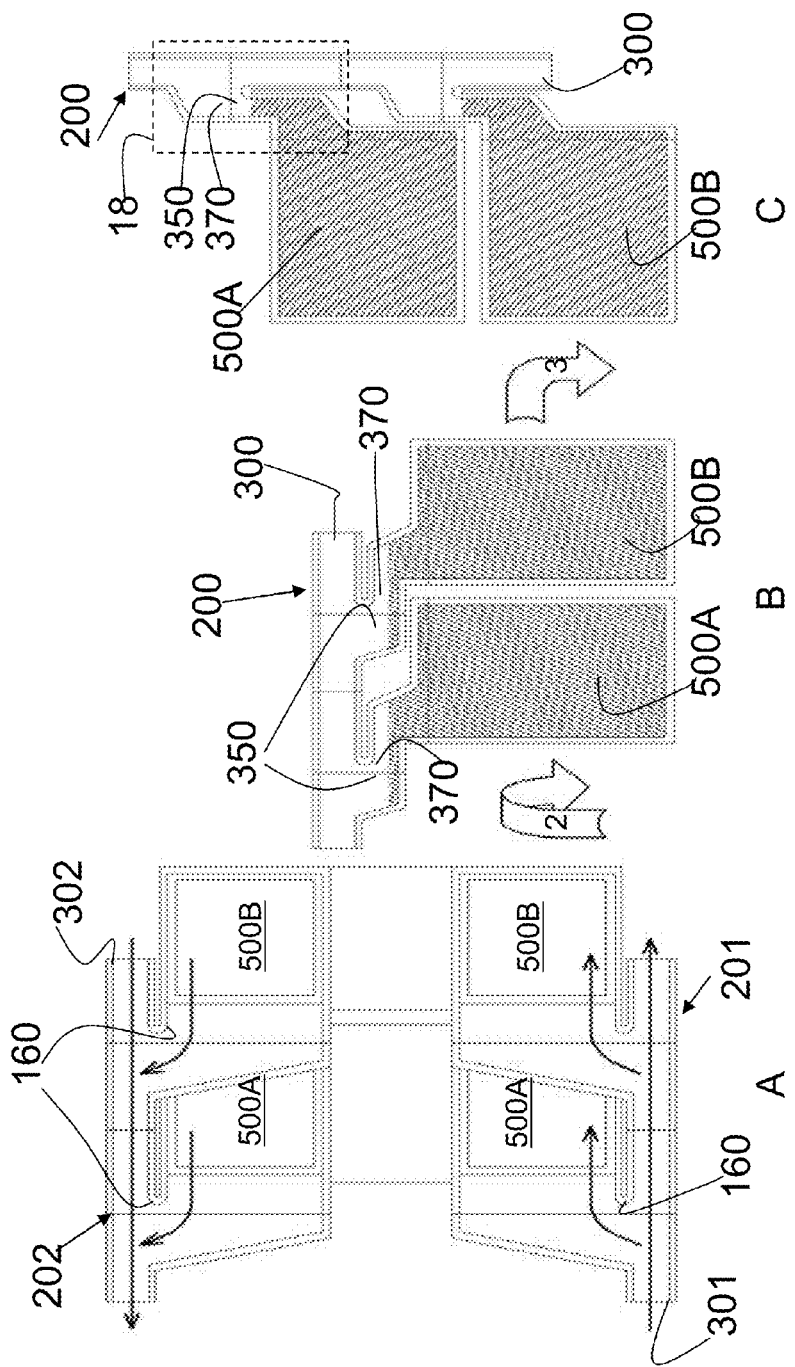
FIGS. 16A, B and C are cross-sectional views taken at slice A, B and B as shown in FIG. 15, respectively.

The manifold can be seen by examining it in cross section. FIG. 15 is a perspective view of the embodiments shown in FIG. 14, illustrating the cross-sections of the apparatus that are shown in FIG. 16.

FIGS. 16A, B and C are cross-sectional views taken at slice A, B and B as shown in FIG. 15, respectively. The arrows shown in FIG. 16A illustrate the flow of liquid into the apparatus through the liquid flow channel of a first manifold 201, and into the culture units 500A and 500B. As liquid enters the cell culture units, 500A and 500B, air escapes through the gas exhaust fluid flow channel 302, as illustrated by the arrows.

In practice, the apparatus may be filled with cell culture media or other liquid as shown in FIG. 16A. In this figure, the apparatus is on its side so that the filling manifold is located on the lowermost portion of the apparatus. In other words, the apparatus may be filled from the bottom, as illustrated in FIG. 16A. Liquid may be introduced using flexible tubing, or by any other means. The fluid may be gravity fed, pumped or be placed under pressure to enter the cell culture apparatus. This is the filling step. Fluid entering the fluid flow channel flows through the manifolds prior to entering the cell culture units. As the fluid volume increases, fluid enters the manifolds from the fluid flow channel through the opening between the manifold and the fluid flow channel. Once fluid enters the manifold, it enters the cell culture units and the cell culture chambers. Fluid enters all of the connected cell culture units in parallel, so filling of manifolds and associated cell culture chambers occurs simultaneously leading to equilibration of the fluid in all chambers. As fluid enters the apparatus through the liquid fluid flow channel, air is displaced from the apparatus through the exhaust fluid flow channel, to the ambient atmosphere. The cell culture chambers may be filled to capacity. For example, if a liquid impermeable gas permeable material is used to form the cell culture chambers, there is no need to retain head space inside the cell culture chambers.

After liquid (illustrated by the cross-hatched area in FIGS. 16B and 16C) has been added to the apparatus, the apparatus may be rotated, as illustrated by the large arrow 2. This is the isolation step. By rotating the apparatus and allowing the liquid to fall into the cell culture units, the apparatus becomes fully filled with liquid. In embodiments, the manifold (now shown in cross-section taken at slice B shown in FIG. 15) has a reservoir 350. This reservoir 350 is a structure that allows the manifold to pool liquid, and form an air gap between the cell culture chambers 500A and 500B and the fluid flow channel 300 of the manifold when the apparatus is in the isolation position as shown in FIG. 16B, or the incubation position, as shown in FIG. 16C. FIG. 16C illustrates the apparatus when it is positioned for cell culture, in the incubation position. After the apparatus has been filled (from the bottom, as shown in FIG. 16A), and rested in the isolation position as shown in FIG. 16B, to allow the apparatus to fill with liquid media, the apparatus can be rotated, as shown in arrow 3, and placed in the incubation position. Once in the incubation position, the apparatus is ready for cell culture. In the incubation position, and in the isolation position, the reservoir 350 is partially filled with liquid (represented by the hatched shading shown in FIG. 16 B and FIG. 16 C), and an air gap 370 has formed between the cell culture units 500A and 500B. This air gap 370 allows isolates the cell culture units and avoids increased hydrostatic pressure in the cell culture chambers contained within the cell culture units.

Figure 17:
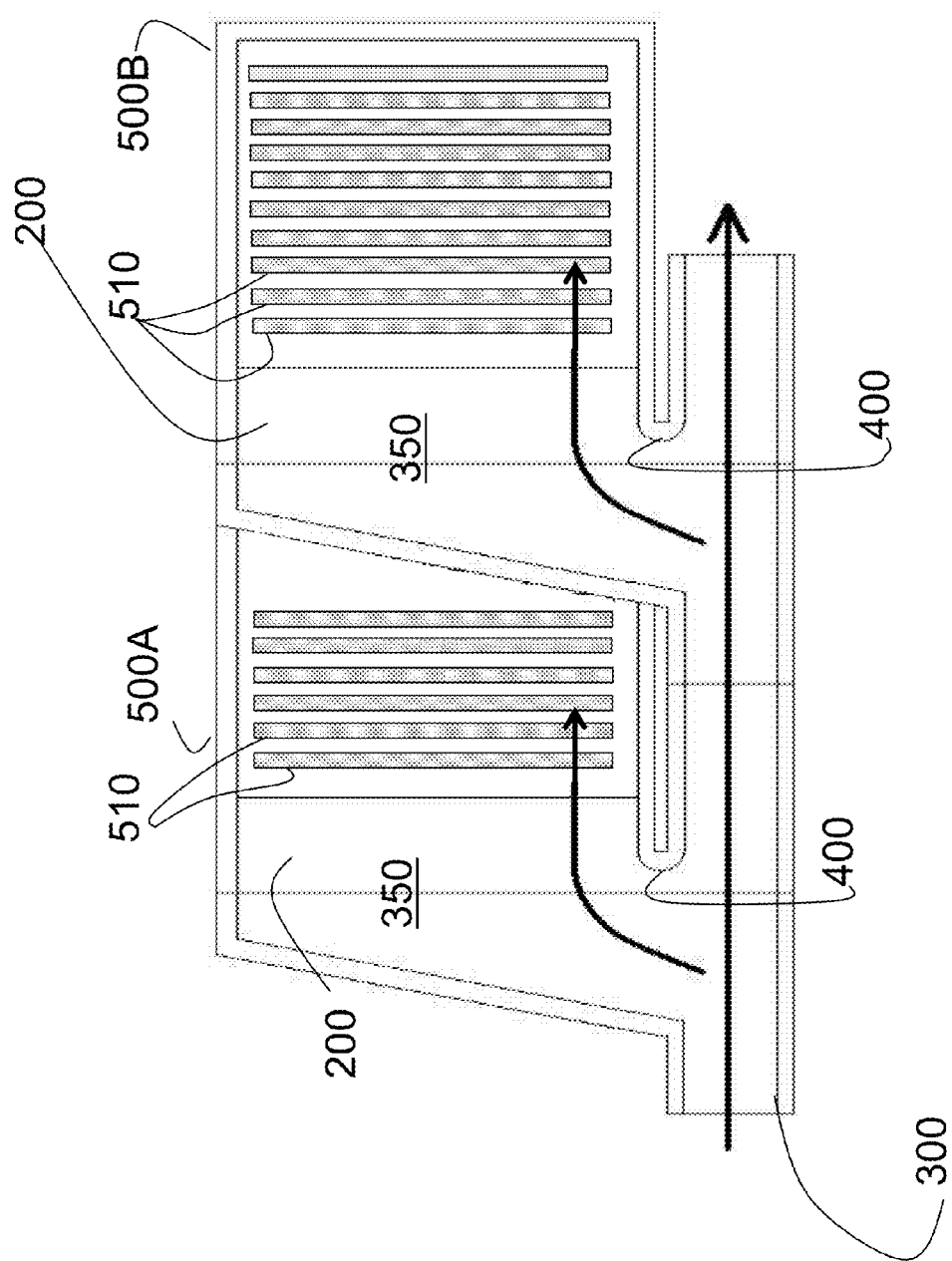
FIG. 17 is an enlarged view of the region shown by dotted line 17 in FIG. 16, illustrating the detail of the port.

FIG. 17 is a schematic illustration of an additional embodiment of the cell culture apparatus, showing the filling of an embodiment of the apparatus (as shown in FIG. 16A). As illustrated in FIG. 17, liquid enters the cell culture units 500A and 500B of the cell culture apparatus from the fluid flow channel 300, through the manifolds 200 which have reservoirs 350. FIG. 17 illustrates that cell culture units 500A and 500B contain cell culture chambers 510. When the apparatus shown in FIG. 17 is oriented in a position for cell culture, in the incubation position, this dam 400 will allow liquid to pool in the cell culture units, while allowing an air gap to remain between the cell culture units 500A and 500B and the fluid flow channel 300. As shown in FIG. 17, the orientation of layers of cell culture surfaces 501. The apparatus is positioned for cell culture when the cell culture chambers 510 are oriented to provide horizontal cell culture surfaces.

Figure 18:
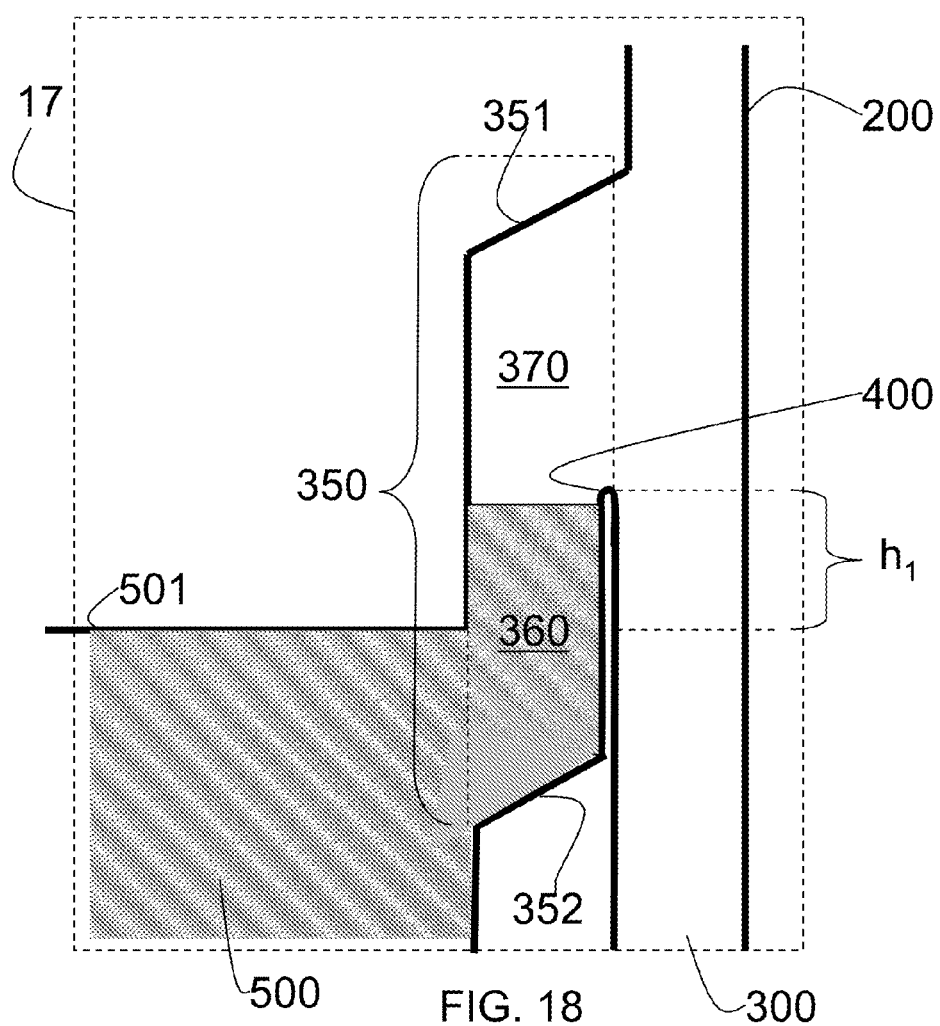
FIG. 18 is a schematic illustration of the filling of an embodiment of the apparatus.

FIG. 18 is an enlarged view of the region shown by dotted line 18 in FIG. 16C, illustrating the detail of the manifold 200, having a reservoir 350, and a fluid flow channel 300. In embodiments, the reservoir is structured and arranged to provide an air space between the culture chamber and the fluid flow channel. In FIG. 18, the reservoir 350 of the manifold 200 is bounded on its top side by a shoulder wall 351, is partially open to the fluid flow channel 300 (as shown by the dashed line) is partially separated from the fluid flow channel 300 by a dam 400, is bounded on its bottom side by wall 352, and is open to the cell culture unit 500 (the boundaries of the reservoir is illustrated by dashed lines). FIG. 18 illustrates that the reservoir 350 of the manifold 200, is open to the fluid flow channel 300, allowing fluid communication between the fluid flow channel 300 and the cell culture chamber 500. In embodiments, the reservoir forms a space in which liquid can pool 360 (represented by the hatched shading shown in FIG. 18), and also allows an air gap 370 to form between the fluid flow channel 300 and the cell culture unit 500. In embodiments, dam 400 extends above the top surface of the connected culture unit 500 by height $h_1$ when the cell culture apparatus is positioned for cell culture. Those of ordinary skill will recognize that height $h_1$ should be large enough to create a liquid pool, even if the cell culture apparatus is moved and disrupted during normal use, but small enough to keep the manifold of a manageable size, permitting the inclusion of a maximum number of cell culture chambers and associated manifolds to be stacked above one another. For example, in embodiments, height $h_1$ may be, for example, 1 mm to 5 cm. Dam 400 allows liquid to pool in the reservoir 350 and allows for the creation of an air gap 370 between the fluid flow channel 300 and the cell culture unit 500 in the manifold 200.

Figure 19:
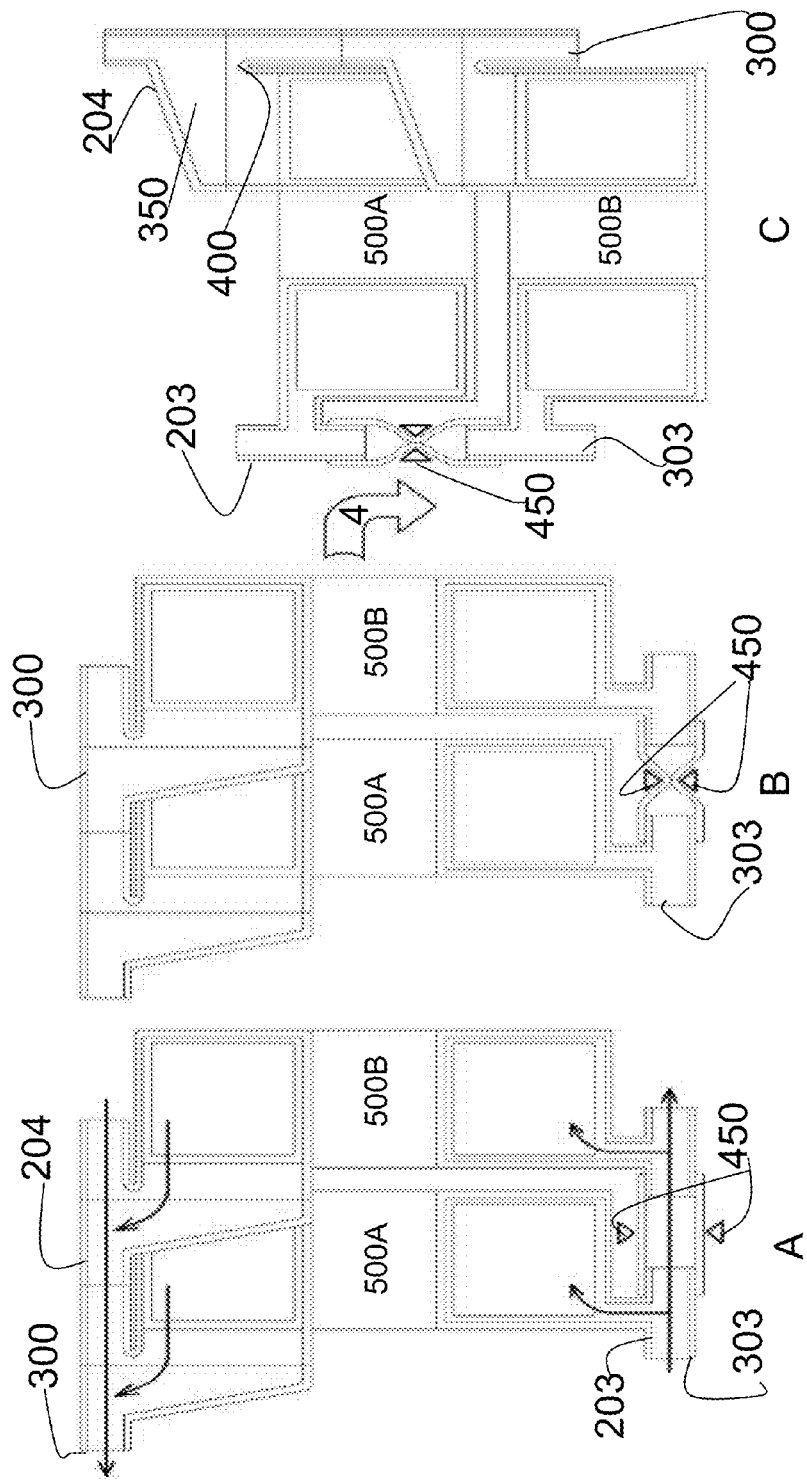
FIGS. 19A, B and C illustrate an embodiment of the apparatus having a valve.

FIGS. 19A, B and C illustrate another embodiment of the apparatus, where the liquid fluid flow channel 303 has a valve 450. Valve 450 is illustrated in an open position in FIG. 19A, and in a closed position in FIG. 19B. As illustrated in FIG. 19A, fluid may enter the cell culture apparatus, as shown by the arrows, from a first manifold 203 of the apparatus, and displaced air may exit the apparatus through a second manifold 204. The first manifold 203, which has a liquid fluid flow channel 303, may have a valve 450. In embodiments, the manifold 203 connected to the liquid fluid flow channel 303 does not have a dam. While a pinch valve is illustrated, in embodiments, the valve may be any type of valve or liquid flow regulator known in the art. In embodiments, the first manifold 203 may be connected to a fluid flow channel 300 and also connected to the cell culture units 500A and 500B to allow fluid communication between the fluid flow channel and the cell culture chambers. The second manifold may have a reservoir 350 and a dam 400 to allow for the pooling of liquid and the formation of an air gap between the fluid flow channel and the cell culture chambers, as shown in FIG. 18 when the apparatus is rotated, as illustrated by arrow 4, to an incubation position. In the embodiments shown in FIG. 19, there are two manifolds, but only one of the manifolds has a dam to create an air gap.

In practice, the valves may be opened, and liquid may be introduced into the apparatus in the filling position as shown in FIG. 19A. Liquid may be introduced into the apparatus. When the cell culture chambers are filled, the valves may be closed and the apparatus may be rotated into the isolation position and then to the incubation position, or, because valves are in place, the apparatus may be rotated directly into the incubation position. In this embodiment, the valves between manifolds creates breaks in the fluid column that would, if left uninterrupted, have lead to increased hydrostatic pressure in the apparatus.

In embodiments, multiple manifolds, and multiple cell culture units may be connected together. Manifolds may be connected together using a connector which may be, for example, tubing or tubing segments, o-rings or other elastomers, compression fittings, adhesive, caulk, or welding processes including laser, ultrasonic, vibration, or other methods known in the art. The connection between manifolds may occur through a number of methods and be permanent or transient.

Figure 20:
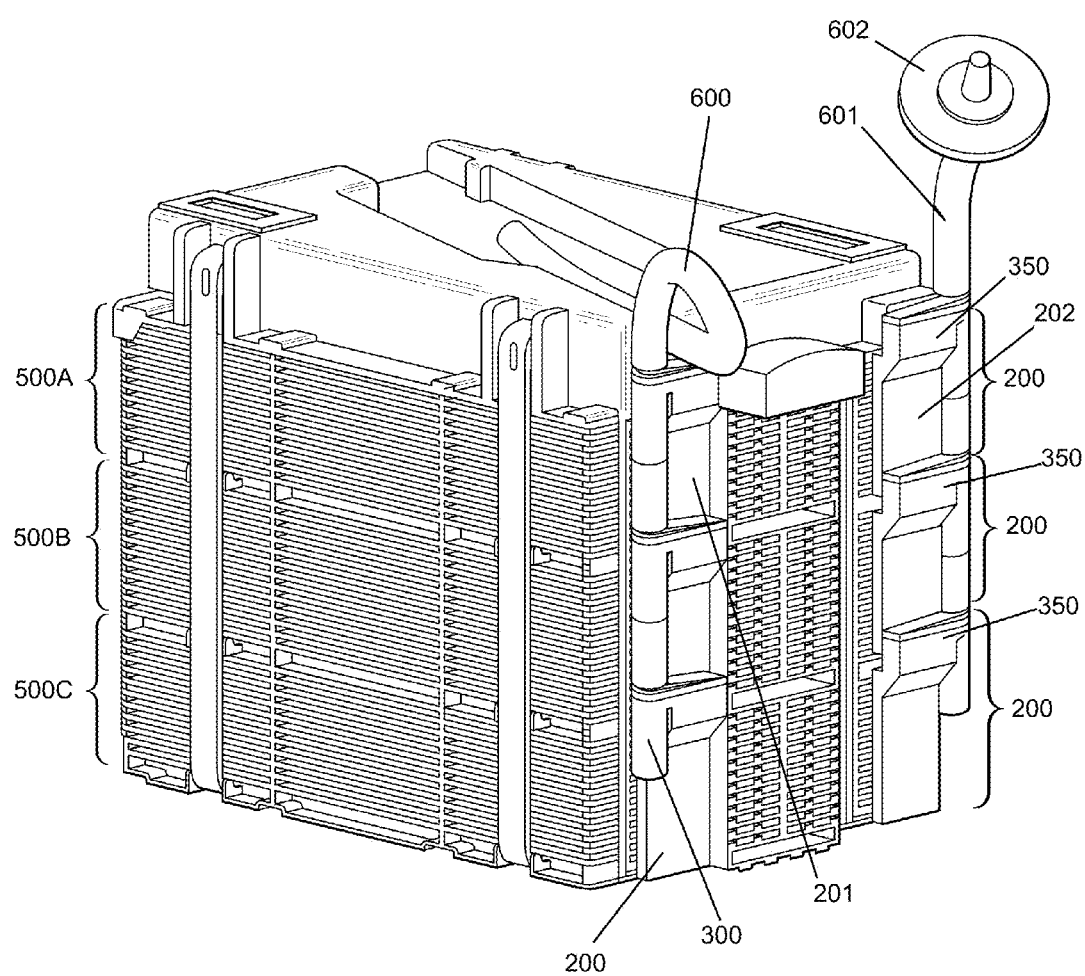
FIG. 20 is a perspective view of an embodiment of the invention.

FIG. 20 is a perspective view of an embodiment of the invention. In this embodiment, three cell culture units, each containing multiple layers of cell culture chambers are stacked, one on top of the other, to form a multiple layer cell culture apparatus. Each cell culture unit 500A, 500B and 500C has two manifolds 200. Liquid may enter the first cell culture unit 500A through the first manifold 201, through tubing 600 and displaced air may exit the first cell culture unit 500A through the second manifold 202 through tubing 601. Tubing may have filters 602. Liquid enters each of the stacked cell culture units in the same manner. Because liquid enters each cell culture unit through the fluid flow channel 300, liquid is delivered to each cell culture unit at the same time, simultaneously, in parallel. Each manifold has a reservoir 350.

Ports and manifolds, or portions thereof, as described herein may be formed from any suitable material. For example, a port, manifold, or component thereof may be formed from a biocompatible polymeric material. In various embodiments, a port or manifold is formed from one or more materials from which a cell culture unit is formed.

It will be understood that a port, manifold, or cell culture unit may be of any suitable size. In many of the depicted embodiments, the ports and components thereof are depicted as having a rectangular cross-sectional shape, but it will be understood that they may have any suitable cross-sectional shape, such as circular, ellipsoidal or the like. It will be further understood that a cell culture unit may include any number of cell culture chambers and that a manifold many include any number of ports. In some embodiments, a cell culture unit has, for example, 10 stacked cell culture chambers per port or 12 stacked cell culture chambers per port, and ten such units are stacked to provide a manifold with 10 ports or 12 ports and a culture system with 100 culture chambers or 120 culture chambers. In embodiments, any number of stacked cell culture chambers may be assembled in cell culture units, providing manifolds with any number of cell culture chambers.

Thus, embodiments of CELL CULTURE SYSTEM WITH MANIFOLD are disclosed. One skilled in the art will appreciate that the cell culture apparatuses and methods described herein can be practiced with embodiments other than those disclosed. The disclosed embodiments are presented for purposes of illustration and not limitation.

What is claimed is:

1. A cell culture apparatus having a cascading manifold, comprising:
    a plurality of cell culture chambers, each cell culture chamber comprising a top surface and a bottom surface and configured to culture cells on the bottom surface, each cell culture chamber comprising gas permeable, liquid impermeable film;
    wherein the plurality of cell culture chambers are stacked one on top of the other to form a stacked cell culture unit, each cell culture unit comprising a manifold;
    a plurality of cell culture units stacked one on top of the other;
    each manifold comprising an inlet, an overflow outlet and a plurality of cell culture chamber openings in fluid communication with each of the plurality of cell culture chambers of a cell culture unit;
    wherein fluid, introduced into a first manifold through the inlet, flows into each cell culture chamber through the plurality of cell culture chamber openings until each cell culture chamber is filled with fluid and then, once each cell culture chamber is filled, the first manifold fills with fluid and fluid flows out of the first manifold through the overflow outlet;
    wherein the overflow outlet of the first manifold of a first cell culture unit is coupled to the inlet of a second manifold of a second cell culture unit;
    wherein fluid flowing out of the first manifold through the overflow outlet flows into the inlet of a second manifold of a second cell culture unit.

2. The cell culture apparatus of claim 1 wherein at least one of the manifold inlets comprises a dam that extends above the elevation of a top surface of a top cell culture chamber of the cell culture unit to which the manifold inlet is attached when the cell culture apparatus is in an incubation position.

3. The cell culture apparatus of claim 2 wherein each cell culture unit further comprises an additional manifold.

4. The cell culture apparatus of claim 3 further comprising tubing attached to the inlets of the topmost manifolds.

5. The cell culture apparatus of claim 3 further comprising spacer layers adjacent to gas permeable, liquid impermeable film and exterior to cell culture chambers.

6. The cell culture apparatus of claim 2 further comprising tubing attached to the inlet of the topmost manifold.

7. The cell culture apparatus of claim 6 further comprising spacer layers adjacent to gas permeable, liquid impermeable film and exterior to cell culture chambers.

8. The cell culture apparatus of claim 2 further comprising spacer layers adjacent to gas permeable, liquid impermeable film and exterior to cell culture chambers.

9. The cell culture apparatus of claim 1 wherein each of the manifold inlets comprises a dam that extends above the elevation of a top surface of a top cell culture chamber of the cell culture unit to which the manifold inlet is attached when the cell culture apparatus is in an incubation position.

10. The cell culture apparatus of claim 9 wherein each cell culture unit further comprises an additional manifold.

11. The cell culture apparatus of claim 10 further comprising tubing attached to the inlets of the topmost manifolds.

12. The cell culture apparatus of claim 10 further comprising spacer layers adjacent to gas permeable, liquid impermeable film and exterior to cell culture chambers.

13. The cell culture apparatus of claim 9 further comprising tubing attached to the inlet of the topmost manifold.

14. The cell culture apparatus of claim 13 further comprising spacer layers adjacent to gas permeable, liquid impermeable film and exterior to cell culture chambers.

15. The cell culture apparatus of claim 9 further comprising spacer layers adjacent to gas permeable, liquid impermeable film and exterior to cell culture chambers.

16. The cell culture apparatus of claim 1 wherein each cell culture unit further comprises an additional manifold.

17. The cell culture apparatus of claim 16 further comprising tubing attached to the inlets of the topmost manifolds.

18. The cell culture apparatus of claim 17 further comprising spacer layers adjacent to gas permeable, liquid impermeable film and exterior to cell culture chambers.

19. The cell culture apparatus of claim 16 further comprising spacer layers adjacent to gas permeable, liquid impermeable film and exterior to cell culture chambers.

20. The cell culture apparatus of claim 1 further comprising tubing attached to the inlet of the topmost manifold.

21. The cell culture apparatus of claim 20 further comprising spacer layers adjacent to gas permeable, liquid impermeable film and exterior to cell culture chambers.

22. The cell culture apparatus of claim 1 further comprising spacer layers adjacent to gas permeable, liquid impermeable film and exterior to cell culture chambers.

* * * * *